(12) United States Patent
Allen et al.

(10) Patent No.: US 11,823,798 B2
(45) Date of Patent: Nov. 21, 2023

(54) CONTAINER-BASED KNOWLEDGE GRAPHS FOR DETERMINING ENTITY RELATIONS IN NON-NARRATIVE TEXT

(71) Applicant: Merative US L.P., Ann Arbor, MI (US)

(72) Inventors: Corville O. Allen, Morrisville, NC (US); Roberto DeLima, Apex, NC (US); Aysu Ezen Can, Cary, NC (US); Robert C. Sizemore, Fuquay-Varina, NC (US)

( * ) Notice: Subject to any disclaimer, the term of this patent is extended or adjusted under 35 U.S.C. 154(b) by 809 days.

(21) Appl. No.: 15/278,875

(22) Filed: Sep. 28, 2016

(65) Prior Publication Data
US 2018/0089382 A1    Mar. 29, 2018

(51) Int. Cl.
*G16H 50/20* (2018.01)
*G16H 10/60* (2018.01)
(Continued)

(52) U.S. Cl.
CPC ........... *G16H 50/20* (2018.01); *G06F 40/205* (2020.01); *G06F 40/253* (2020.01);
(Continued)

(58) Field of Classification Search
CPC ........ G16H 10/00; G16H 10/40; G16H 15/00; G16H 20/00; G16H 20/10; G16H 20/13;
(Continued)

(56) References Cited

U.S. PATENT DOCUMENTS

| 6,516,308 B1 * | 2/2003 | Cohen ............... G06F 17/30569 706/12 |
| 8,249,344 B2 | 8/2012 | Viola et al. |

(Continued)

OTHER PUBLICATIONS

Kulandai et al., "Ontology based EMR for decision making in health care using SNOMED CT," 2012 International Conference on Recent Trends in Information Technology, Chennai, India, 2012, pp. 514-519, doi: 10.1109/ICRTIT.2012.6206787.*

(Continued)

*Primary Examiner* — Robert W Morgan
*Assistant Examiner* — Charles P Coleman
(74) *Attorney, Agent, or Firm* — Stephen J. Walder, Jr.

(57) ABSTRACT

A mechanism is provided in a data processing system comprising least one processor and at least one memory, the at least one memory comprising instructions executed by the at least one processor to cause the at least one processor to implement a clinical decision support system. The mechanism receives a plurality of patient electronic medical records (EMRs) for a patient from a plurality of different sources. For a portion of a patient EMR record of the plurality of patient EMRs, the mechanism detects entities and analyzes a document structure of the portion of the patient EMR to identify a hierarchical structure of the portion of the patient EMR. The mechanism generates a container representation of the portion of the patient EMR based on the hierarchical structure. The mechanism placing each of the one or more sentences within the container representation based on relative position within the hierarchical structure. The mechanism generates a knowledge graph using the detected entities and the container representation.

20 Claims, 7 Drawing Sheets

(51) Int. Cl.
| | |
|---|---|
| *G16H 70/00* | (2018.01) |
| *G16H 50/70* | (2018.01) |
| *G06F 40/205* | (2020.01) |
| *G06F 40/253* | (2020.01) |
| *G06F 40/284* | (2020.01) |
| *G06F 40/295* | (2020.01) |

(52) U.S. Cl.
CPC .......... *G06F 40/284* (2020.01); *G06F 40/295* (2020.01); *G16H 10/60* (2018.01); *G16H 50/70* (2018.01); *G16H 70/00* (2018.01)

(58) Field of Classification Search
CPC ........ G16H 20/17; G16H 30/00; G16H 40/00; G16H 50/00; G16H 70/00; G16H 80/00; G16H 50/20; G16H 10/60; G06F 17/2705; G06F 17/274; G06F 17/277; G06F 17/278
USPC .................................................. 705/2, 3, 20
See application file for complete search history.

(56) References Cited

U.S. PATENT DOCUMENTS

| | | | |
|---|---|---|---|
| 8,275,803 B2 | 9/2012 | Brown et al. | |
| 8,335,754 B2 | 12/2012 | Dawson et al. | |
| 2004/0024739 A1* | 2/2004 | Copperman | G06F 16/353 |
| 2005/0138000 A1 | 6/2005 | Roux et al. | |
| 2005/0138005 A1 | 6/2005 | Roux et al. | |
| 2006/0280370 A1* | 12/2006 | Viola | G06K 9/726 |
| | | | 382/229 |
| 2007/0003147 A1* | 1/2007 | Viola | G06F 40/211 |
| | | | 382/229 |
| 2007/0033221 A1* | 2/2007 | Copperman | G06F 16/367 |
| 2009/0089095 A1* | 4/2009 | Esham | G16H 10/60 |
| | | | 705/3 |
| 2009/0287678 A1 | 11/2009 | Brown et al. | |
| 2010/0228693 A1* | 9/2010 | Dawson | G06F 17/2705 |
| | | | 706/12 |
| 2011/0066587 A1 | 3/2011 | Ferrucci et al. | |
| 2011/0125528 A1* | 5/2011 | Padate | G06Q 50/24 |
| | | | 705/3 |
| 2011/0125734 A1 | 5/2011 | Duboue et al. | |
| 2012/0215560 A1* | 8/2012 | Ofek | G16H 10/00 |
| | | | 705/3 |
| 2012/0246105 A1* | 9/2012 | James | G16H 40/20 |
| | | | 706/47 |
| 2013/0007055 A1 | 1/2013 | Brown et al. | |
| 2013/0018652 A1 | 1/2013 | Ferrucci et al. | |
| 2013/0054512 A1* | 2/2013 | Ephrat | G16H 40/67 |
| | | | 707/602 |
| 2013/0066886 A1 | 3/2013 | Bagchi et al. | |
| 2013/0290020 A1* | 10/2013 | Brush | G06Q 50/24 |
| | | | 705/3 |
| 2014/0149132 A1* | 5/2014 | DeHaan | G16H 10/60 |
| | | | 705/2 |
| 2014/0281982 A1* | 9/2014 | Clark | G06F 3/0481 |
| | | | 715/716 |
| 2014/0365507 A1* | 12/2014 | Wissner | G06F 17/30893 |
| | | | 707/748 |
| 2016/0132648 A1* | 5/2016 | Shah | G06F 19/325 |
| | | | 705/2 |
| 2018/0082183 A1* | 3/2018 | Hertz | G06F 16/9024 |
| 2018/0107801 A1* | 4/2018 | Guo | G16H 15/00 |

OTHER PUBLICATIONS

Szenasi et al., "Concept extraction from medical documents a contextual approach," 2015 IEEE International Conference on Intelligent Computer Communication and Processing (ICCP), Cluj-Napoca, Romania, 2015, pp. 13-17, doi: 10.1109/ICCP.2015.7312599.*

Iqbal et al., "An Ontology-Based Electronic Medical Record for Chronic Disease Management," 2011 44th Hawaii International Conference on System Sciences, Kauai, HI, USA, 2011, pp. 1-10, doi: 10.1109/HICSS.2011.61.*

List of IBM Patents or Patent Applications Treated as Related, Oct. 18, 2016, 2 pages.

Galitsky, Boris, "Learning parse structure of paragraphs and its applications in search", Elsevier, http://www.sfbayacm.org/sites/default/files/learningparsestructureparagraph.pdf, Engineering Applications of Artificial Intelligence, Feb. 23, 2014, 25 pages.

Gesmundo, Andrea et al., "Projecting the Knowledge Graph to Syntactic Parsing", Google, http://static.googleusercontent.com/media/research.google.com/en//pubs/archive/42254.pdf, Apr. 26, 2014, 5 pages.

Hakkani-Tur, Dilek et al., "Using a Knowledge Graph and Query Click Logs for Unsupervised Learning of Relation Detection", IEEE, http://www.msr-waypoint.com/pubs/185271/ICASSP13-KG.pdf, International Conference on Acoustics, Speech, and Signal Processing, ICASSP 2013, May 1, 2013, pp. 8327-8331.

High, Rob, "The Era of Cognitive Systems: An Inside Look at IBM Watson and How it Works", IBM Corporation, Redbooks, Dec. 12, 2012, 16 pages.

Lee, Noah et al., "Mining electronic medical records to explore the linkage between healthcare resource utilization and disease severity in diabetic patients", IEEE, IEEE Computer Society, 2011 First IEEE Conference on Healthcare Informatics, Imaging and Systems Biology, Jul. 26, 2011, pp. 250-257.

Mccord, M.C. et al., "Deep parsing in Watson", IBM J. Res. & Dev. vol. 56 No. 3/4 Paper 3, May/Jul. 2012, pp. 3:1-3:15.

Muller, R. et al., "A Graph-Grammar Approach to Represent Context Knowledge in Oncological Patient Records", Dutch Society for Medical Informatics, Strategic Alliances between Patient Documentation and Medical Informatics, Proceedings of AMICE95, Amsterdam, Nov. 1995, pp. 335-348.

Voskarides, Nikos et al., "Learning to Explain Entity Relationships in Knowledge Graphs", Association for Computational Linguistics, http://www.aclweb.org/anthology/P15-1055, Proceedings of the 53rd Annual Meeting of the Association for Computational Linguistics and the 7th International Joint Conference on Natural Language Processing, Beijing, China, Jul. 26-31, 2015, pp. 564-574.

Yu, Tong et al., "Semantic Graph Mining for e-Science", Association for the Advancement of Artificial Intelligence, AAAI Conference on Artificial Intelligence and Interactive Digital Entertainment 2007, May 11, 2007, pp. 77-80.

Yuan, Michael J., "Watson and healthcare, How natural language processing and semantic search could revolutionize clinical decision support", IBM developerWorks, IBM Corporation, Apr. 12, 2011, 14 pages.

De la Villa, Manuel, et al., A Learning Support Tool with Clinical Cases Based on Concept Maps and Medical Entity Recognition, Proceedings of the 2012 ACM International Conference on Intelligent User Interfaces, ACM Feb. 14-17, 2012, 10 pages.

* cited by examiner

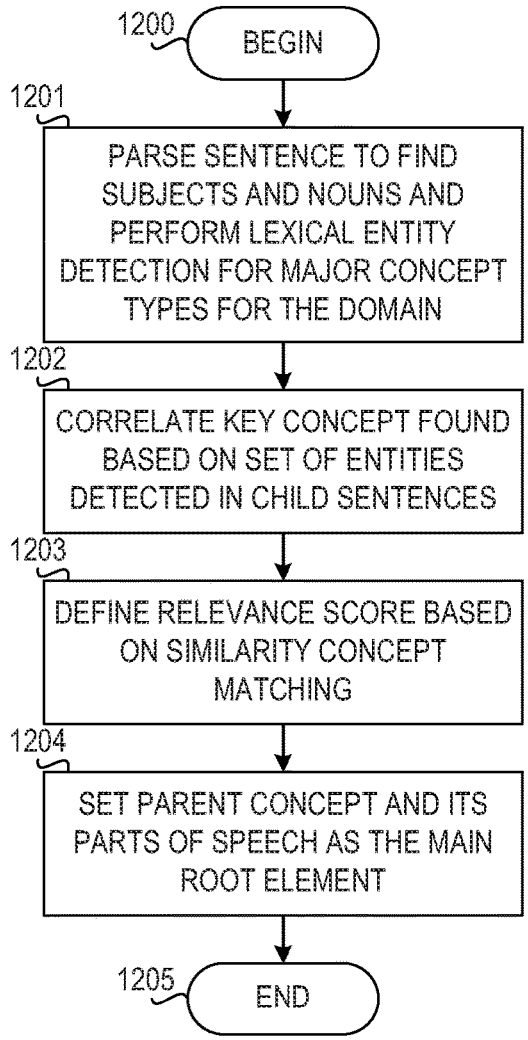
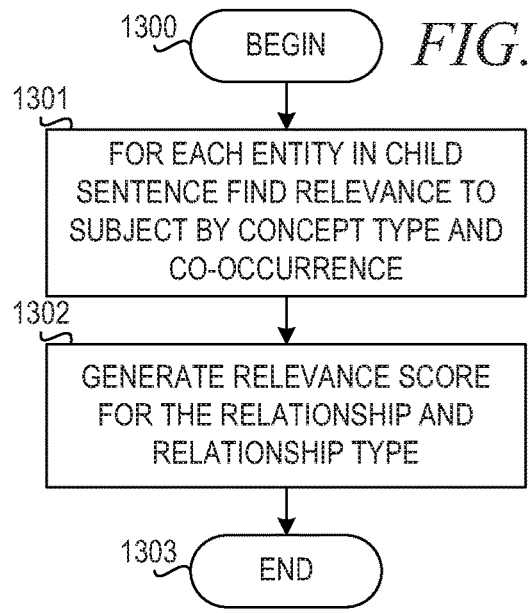
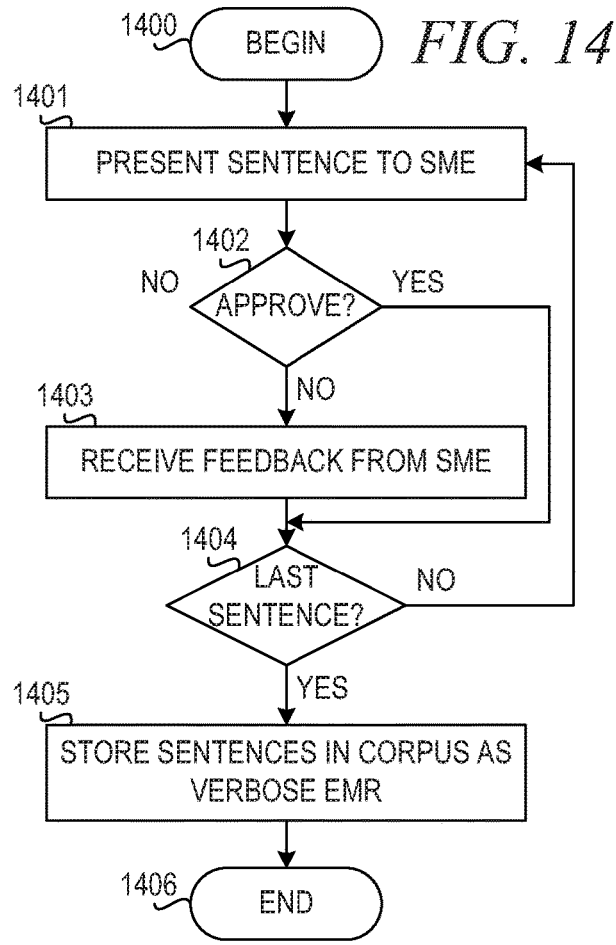

CONTAINER-BASED KNOWLEDGE GRAPHS FOR DETERMINING ENTITY RELATIONS IN NON-NARRATIVE TEXT

BACKGROUND

The present application relates generally to an improved data processing apparatus and method and more specifically to mechanisms for container-based knowledge graphs for determining entity relations in non-narrative text.

Decision-support systems exist in many different industries where human experts require assistance in retrieving and analyzing information. An example that will be used throughout this application is a diagnosis system employed in the healthcare industry. Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations. The MYCIN system for diagnosing infectious diseases, also developed in the 1970s, uses structured knowledge in the form of production rules, stating that if certain facts are true, then one can conclude certain other facts with a given certainty factor. DXplain, developed starting in the 1980s, uses structured knowledge similar to that of Internist-I, but adds a hierarchical lexicon of findings.

Iliad, developed starting in the 1990s, adds more sophisticated probabilistic reasoning where each disease has an associated a priori probability of the disease (in the population for which Iliad was designed), and a list of findings along with the fraction of patients with the disease Who have the finding (sensitivity), and the fraction of patients without the disease who have the finding (1-specificity).

In 2000, diagnosis systems using unstructured knowledge started to appear. These systems use some structuring of knowledge such as, for example, entities such as findings and disorders being tagged in documents to facilitate retrieval. ISABEL, for example, uses Autonomy information retrieval software and a database of medical textbooks to retrieve appropriate diagnoses given input findings. Autonomy Auminence uses the Autonomy technology to retrieve diagnoses given findings and organizes the diagnoses by body system. First CONSULT allows one to search a large collection of medical books, journals, and guidelines by chief complaints and age group to arrive at possible diagnoses. PEPID DDX is a diagnosis generator based on PEPID's independent clinical content.

Clinical decision rules have been developed for a number of medical disorders, and computer systems have been developed to help practitioners and patients apply these rules. The Acute Cardiac ischemia Time-Insensitive Predictive Instrument (ACI-TIPI) takes clinical and ECG features as input and produces probability of acute cardiac ischemia as output to assist with triage of patients with chest pain or other symptoms suggestive of acute cardiac ischemia. ACI-TIPI is incorporated into many commercial heart monitors/defibrillators. The CaseWalker system uses a four-item questionnaire to diagnose major depressive disorder. The PKC Advisor provides guidance on 98 patient problems such as abdominal pain and vomiting.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising at least one processor and at least one memory, the at least one memory comprising instructions executed by the at least one processor to cause the at least one processor to implement a clinical decision support system. The method comprises receiving a plurality of patient electronic medical records (EMRs) for a patient from a plurality of different sources. The method further comprises for a portion of a patient EMR record of the plurality of patient EMRs, detecting entities and analyzing a document structure of the portion of the patient EMR to identify a hierarchical structure of the portion of the patient EMR. The method further comprises generating a container representation of the portion of the patient EMR based on the hierarchical structure. The method further comprises placing each of the one or more sentences within the container representation based on relative position within the hierarchical structure. The method further comprises generating a knowledge graph using the detected entities and the container representation.

In other illustrative embodiments, a computer program product comprising a computer usable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 12 is a flowchart illustrating operation of a mechanism for denoting the parent in the hierarchical list and finding the main subject or concept type in accordance with an illustrative embodiment;

FIG. 13 is a flowchart illustrating operation of a mechanism for deducing potential relationships to a container level concept in accordance with an illustrative embodiment; and FIG. 14 is a flowchart illustrating operation of a mechanism for generating a verbose electronic medical record in accordance with an illustrative embodiment.

DETAILED DESCRIPTION

Figure 1:
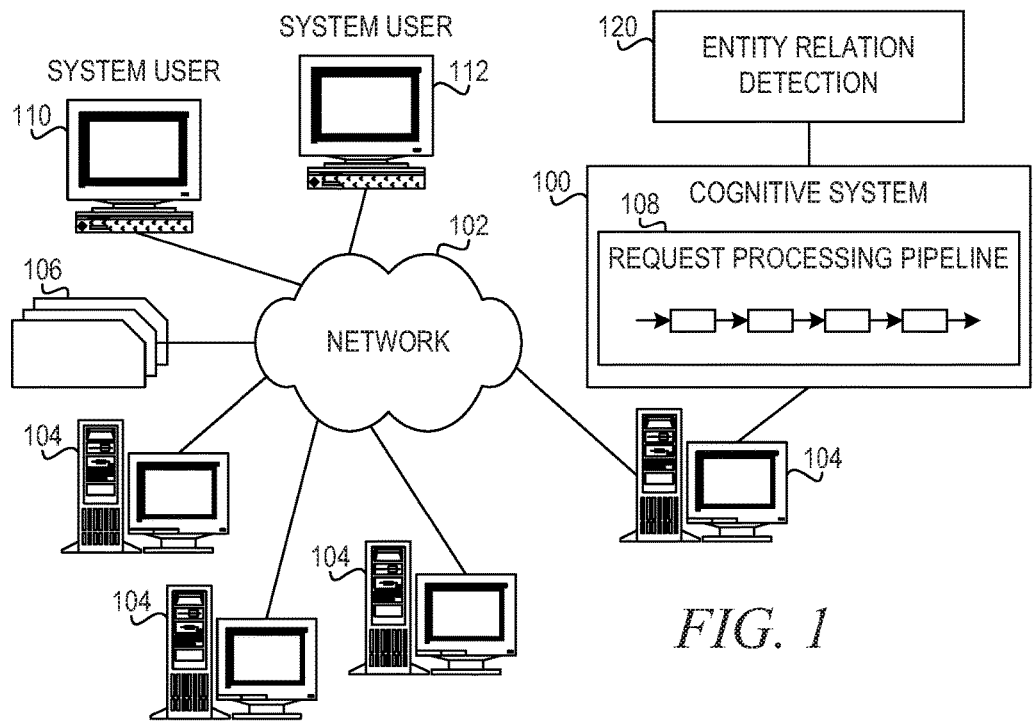
FIG. 1 depicts a schematic diagram of one illustrative embodiment of a cognitive system in a computer network.

Entity detection is an important part of natural language processing for medical text where important concepts are extracted from patient notes in the form of entities with normalized features to be used in clinical decisions. The more accurate the entity detection becomes, the better understanding a clinical decision support system has of the medical text. Therefore, entity detection significantly helps intelligent systems to improve their artificial intelligence power.

State-of-the art entity detection mostly utilizes machine learning models trained on labeled data or are based on lexical matches on a sentence level. However, in medical text most of the entities are related across sentences, and most of the time it is costly to obtain gold standard for these entity relationships. Manual labeling is required for building up a corpus of entity relationships, and it is labor-intensive to create and keep such a corpus up-to-date as new patient cases come in. The illustrative embodiments provide an automated approach that works across sentences and does not require manual intervention.

The illustrative embodiments provide a mechanism that enhances the set of entity relationships by connecting multiple sentences and drawing a knowledge graph based on document structure. The mechanisms of the illustrative embodiments draw a hierarchy of containers to be able to identify entities that are related to each other and draw a higher level picture for the patient case rather than working on a sentence level.

The mechanisms of the illustrative embodiments take a non-standard set of sentences that are in non-obvious form (e.g., lists, sub-sections, hierarchical structures) and dynamically represent the relationships across the sentences with their key relational metadata. This produces a set of knowledge representations that are usually not provided in such a manner in texts and allows for reasoning and conjectures in decision making. This is particularly useful in medical texts in electronic medical records (EMRs) for which understanding relationships is required to reason and provide decision support.

The mechanisms of the illustrative embodiments obtain complete entities from non-standard forms of texts, which is very useful in medical texts and short-hand reports. Disease treatment systems can have better accuracy and utilize reports and forms to provide decision support (oncology, diabetes, lung, advisors).

While the embodiments described herein illustrate a clinical decision support system or a question answering system, the aspects of the embodiments may be applied to any non-narrative text that is arranged in a non-standard form. Examples of non-narrative text may include journal notes, whiteboards, presentation slideshows, packing lists, and the like. For instance, researchers may make lab notes available, and these lab notes may contain rich information. However, the lab notes are not written in full sentences, paragraphs, chapters, etc. Rather, non-narrative forms of text may include numbered lists, bullet lists, box diagrams with text, flowcharts containing text, and the like.

The mechanisms of the illustrative embodiments generate a container representation of a document that includes non-narrative text such as numbered lists, bullet lists, and the like. The mechanisms then generate a knowledge graph and determine relationships between entities using the container representation.

The embodiments are described below with reference to a question answering (QA) system; however, aspects of the illustrative embodiments may apply to other embodiments, such as decision support systems, analytics, data visualization, social media, search engine indexing, etc. The embodiments are described with respect to the medical domain, in particular electronic medical records; however, aspects of the embodiments may apply in other domains and other types of documents with structured and unstructured content. Application of aspects of the illustrative embodiments to other embodiments is within the scope of the present invention.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a," "at least one of," and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "component," if used herein with regard to describing embodiments and features of the invention, is not intended to be limiting of any particular implementation for accomplishing and/or performing the actions, steps, processes, etc., attributable to and/or performed by the component. A component may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular component is, unless otherwise specified, for purposes of convenience of reference and not intended to be limiting to a specific implementation. Additionally, any functionality attributed to a component may be equally performed by multiple components, incorporated into and/or combined with the functionality of another component of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The illustrative embodiments may be utilized in many different types of data processing environments. In order to provide a context for the description of the specific elements and functionality of the illustrative embodiments, FIGS. 1-4 are provided hereafter as example environments in which aspects of the illustrative embodiments may be implemented. It should be appreciated that FIGS. 1-4 are only examples and are not intended to assert or imply any limitation with regard to the environments in which aspects or embodiments of the present invention may be implemented. Many modifications to the depicted environments may be made without departing from the spirit and scope of the present invention.

FIGS. 1-4 are directed to describing an example cognitive system for healthcare applications (also referred to herein as a "healthcare cognitive system") which implements a request processing pipeline, such as a Question Answering (QA) pipeline (also referred to as a Question/Answer pipeline or Question and Answer pipeline) for example, request processing methodology, and request processing computer program product with which the mechanisms of the illustrative embodiments are implemented. These requests may be provided as structured or unstructured request messages, natural language questions, or any other suitable format for requesting an operation to be performed by the healthcare cognitive system. As described in more detail hereafter, the particular healthcare application that is implemented in the cognitive system of the present invention is a healthcare application for providing medical treatment recommendations for patients based on their specific features as obtained from various sources, e.g., patient electronic medical records (EMRs), patient questionnaires, etc. In particular, the mechanisms of the present invention provide a mechanism for verification of clinical hypothetical statements based on dynamic cluster analysis.

It should be appreciated that the healthcare cognitive system, while shown as having a single request processing pipeline in the examples hereafter, may in fact have multiple request processing pipelines. Each request processing pipeline may be separately trained and/or configured to process requests associated with different domains or be configured to perform the same or different analysis on input requests (or questions in implementations using a QA pipeline), depending on the desired implementation. For example, in some cases, a first request processing pipeline may be trained to operate on input requests directed to a first medical malady domain (e.g., various types of blood diseases) while another request processing pipeline may be trained to answer input requests in another medical malady domain (e.g., various types of cancers). In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have its own associated corpus or corpora that it ingests and operates on, e.g., one corpus for blood disease domain documents and another corpus for cancer diagnostics domain related documents in the above examples. In some cases, the request processing pipelines may each operate on the same domain of input questions but may have different configurations, e.g., different annotators or differently trained annotators, such that different analysis and potential answers are generated. The healthcare cognitive system may provide additional logic for routing input requests to the appropriate request processing pipeline, such as based on a determined domain of the input request, combining and evaluating final results generated by the processing performed by multiple request processing pipelines, and other control and interaction logic that facilitates the utilization of multiple request processing pipelines.

As noted above, one type of request processing pipeline with which the mechanisms of the illustrative embodiments may be utilized is a Question Answering (QA) pipeline. The description of example embodiments of the present invention hereafter will utilize a QA pipeline as an example of a request processing pipeline that may be augmented to include mechanisms in accordance with one or more illustrative embodiments. It should be appreciated that while the present invention will be described in the context of the cognitive system implementing one or more QA pipelines that operate on an input question, the illustrative embodiments are not limited to such. Rather, the mechanisms of the illustrative embodiments may operate on requests that are not posed as "questions" but are formatted as requests for the cognitive system to perform cognitive operations on a specified set of input data using the associated corpus or corpora and the specific configuration information used to configure the cognitive system. For example, rather than asking a natural language question of "What diagnosis applies to patient P?" the cognitive system may instead receive a request of "generate diagnosis for patient P," or the like. It should be appreciated that the mechanisms of the QA system pipeline may operate on requests in a similar manner to that of input natural language questions with minor modifications. In fact, in some cases, a request may be converted to a natural language question for processing by the QA system pipelines if desired for the particular implementation.

As will be discussed in greater detail hereafter, the illustrative embodiments may be integrated in, augment, and extend the functionality of these QA pipeline, or request processing pipeline, mechanisms of a healthcare cognitive system with regard to providing a medical malady independent treatment recommendation system which may receive an input question regarding the recommended treatment for a specific patient and may utilize the QA pipeline mechanisms to evaluate patient information and other medical information in one or more corpora of medical information to determine the most appropriate treatment for the specific patient.

Thus, it is important to first have an understanding of how cognitive systems and question and answer creation in a cognitive system implementing a QA pipeline are implemented before describing how the mechanisms of the illustrative embodiments are integrated in and augment such cognitive systems and request processing pipeline, or QA pipeline, mechanisms. It should be appreciated that the mechanisms described in FIGS. 1-4 are only examples and are not intended to state or imply any limitation with regard to the type of cognitive system mechanisms with which the illustrative embodiments are implemented. Many modifications to the example cognitive system shown in FIGS. 1-4 may be implemented in various embodiments of the present invention without departing from the spirit and scope of the present invention.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

Navigate the complexities of human language and understanding
Ingest and process vast amounts of structured and unstructured data
Generate and evaluate hypothesis
Weigh and evaluate responses that are based only on relevant evidence
Provide situation-specific advice, insights, and guidance
Improve knowledge and learn with each iteration and interaction through machine learning processes
Enable decision making at the point of impact (contextual guidance)
Scale in proportion to the task
Extend and magnify human expertise and cognition.
Identify resonating, human-like attributes and traits from natural language
Deduce various language specific or agnostic attributes from natural language
High degree of relevant recollection from data points (images, text, voice) (memorization and recall)
Predict and sense with situational awareness that mimic human cognition based on experiences
Answer questions based on natural language and specific evidence In one aspect, cognitive systems provide mechanisms for answering questions posed to these cognitive systems using a Question Answering pipeline or system (QA system) and/or process requests which may or may not be posed as natural language questions. The QA pipeline or system is an artificial intelligence application executing on data processing hardware that answers questions pertaining to a given subject-matter domain presented in natural language. The QA pipeline receives inputs from various sources including input over a network, a corpus of electronic documents or other data, data from a content creator, information from one or more content users, and other such inputs from other possible sources of input. Data storage devices store the corpus of data. A content creator creates content in a document for use as part of a corpus of data with the QA pipeline. The document may include any file, text, article, or source of data for use in the QA system. For example, a QA pipeline accesses a body of knowledge about the domain, or subject matter area, e.g., financial domain, medical domain, legal domain, etc., where the body of knowledge (knowledgebase) can be organized in a variety of configurations, e.g., a structured repository of domain-specific information, such as ontologies, or unstructured data related to the domain, or a collection of natural language documents about the domain.

Content users input questions to the cognitive system, which implements the QA pipeline. The QA pipeline then answers the input questions using the content in the corpus of data by evaluating documents, sections of documents, portions of data in the corpus, or the like. When a process evaluates a given section of a document for semantic content, the process can use a variety of conventions to query such document from the QA pipeline, e.g., sending the query to the QA pipeline as a well-formed question which is then interpreted by the QA pipeline and a response is provided containing one or more answers to the question. Semantic content is content based on the relation between signifiers, such as words, phrases, signs, and symbols, and what they stand for, their denotation, or connotation. In other words, semantic content is content that interprets an expression, such as by using Natural Language Processing.

As will be described in greater detail hereafter, the QA pipeline receives an input question, parses the question to extract the major features of the question, uses the extracted features to formulate queries, and then applies those queries to the corpus of data. Based on the application of the queries to the corpus of data, the QA pipeline generates a set of hypotheses, or candidate answers to the input question, by looking across the corpus of data for portions of the corpus of data that have some potential for containing a valuable response to the input question. The QA pipeline then performs deep analysis on the language of the input question and the language used in each of the portions of the corpus of data found during the application of the queries using a variety of reasoning algorithms. There may be hundreds or even thousands of reasoning algorithms applied, each of which performs different analysis, e.g., comparisons, natural language analysis, lexical analysis, or the like, and generates a score. For example, some reasoning algorithms may look at the matching of terms and synonyms within the language of the input question and the found portions of the corpus of data. Other reasoning algorithms may look at temporal or spatial features in the language, while others may evaluate the source of the portion of the corpus of data and evaluate its veracity.

The scores obtained from the various reasoning algorithms indicate the extent to which the potential response is inferred by the input question based on the specific area of focus of that reasoning algorithm. Each resulting score is then weighted against a statistical model. The statistical model captures how well the reasoning algorithm preformed at establishing the inference between two similar passages for a particular domain during the training period of the QA pipeline. The statistical model is used to summarize a level of confidence that the QA pipeline has regarding the evidence that the potential response, i.e. candidate answer, is inferred by the question. This process is repeated for each of the candidate answers until the QA pipeline identifies candidate answers that surface as being significantly stronger than others and thus, generates a final answer, or ranked set of answers, for the input question.

As mentioned above, QA pipeline mechanisms operate by accessing information from a corpus of data or information (also referred to as a corpus of content), analyzing it, and then generating answer results based on the analysis of this data. Accessing information from a corpus of data typically includes: a database query that answers questions about what is in a collection of structured records, and a search that delivers a collection of document links in response to a query against a collection of unstructured data (text, markup language, etc.). Conventional question answering systems are capable of generating answers based on the corpus of data and the input question, verifying answers to a collection of questions for the corpus of data, correcting errors in digital text using a corpus of data, and selecting answers to questions from a pool of potential answers, i.e. candidate answers.

Content creators, such as article authors, electronic document creators, web page authors, document database creators, and the like, determine use cases for products, solutions, and services described in such content before writing their content. Consequently, the content creators know what questions the content is intended to answer in a particular topic addressed by the content. Categorizing the questions, such as in terms of roles, type of information, tasks, or the like, associated with the question, in each document of a corpus of data allows the QA pipeline to more quickly and efficiently identify documents containing content related to a specific query. The content may also answer other questions that the content creator did not contemplate that may be useful to content users. The questions and answers may be verified by the content creator to be contained in the content for a given document. These capabilities contribute to improved accuracy, system performance, machine learning, and confidence of the QA pipeline. Content creators, automated tools, or the like, annotate or otherwise generate metadata for providing information useable by the QA pipeline to identify these questions and answer attributes of the content.

Operating on such content, the QA pipeline generates answers for input questions using a plurality of intensive analysis mechanisms which evaluate the content to identify the most probable answers, i.e. candidate answers, for the input question. The most probable answers are output as a ranked listing of candidate answers ranked according to their relative scores or confidence measures calculated during evaluation of the candidate answers, as a single final answer having a highest ranking score or confidence measure, or which is a best match to the input question, or a combination of ranked listing and final answer.

FIG. 1 depicts a schematic diagram of one illustrative embodiment of a cognitive system 100 implementing a request processing pipeline 108, which in some embodiments may be a question answering (QA) pipeline, in a computer network 102. For purposes of the present description, it will be assumed that the request processing pipeline 108 is implemented as a QA pipeline that operates on structured and/or unstructured requests in the form of input questions. One example of a question processing operation which may be used in conjunction with the principles described herein is described in U.S. Patent Application Publication No. 2011/0125734, which is herein incorporated by reference in its entirety.

The cognitive system 100 is implemented on one or more computing devices 104 (comprising one or more processors and one or more memories, and potentially any other computing device elements generally known in the art including buses, storage devices, communication interfaces, and the like) connected to the computer network 102. The network 102 includes multiple computing devices 104 in communication with each other and with other devices or components via one or more wired and/or wireless data communication links, where each communication link comprises one or more of wires, routers, switches, transmitters, receivers, or the like. The cognitive system 100 and network 102 enables question processing and answer generation (QA) functionality for one or more cognitive system users via their respective computing devices 110-112. Other embodiments of the cognitive system 100 may be used with components, systems, sub-systems, and/or devices other than those that are depicted herein.

The cognitive system 100 is configured to implement a request processing pipeline 108 that receive inputs from various sources. For example, the cognitive system 100 receives input from the network 102, a corpus of electronic documents 106, cognitive system users, and/or other data and other possible sources of input. In one embodiment, some or all of the inputs to the cognitive system 100 are routed through the network 102. The various computing devices 104 on the network 102 include access points for content creators and QA system users. Some of the computing devices 104 include devices for a database storing the corpus of data 106 (which is shown as a separate entity in FIG. 1 for illustrative purposes only). Portions of the corpus of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input questions to the cognitive system 100 that are answered by the content in the corpus of data 106. In one embodiment, the questions are formed using natural language. The cognitive system 100 parses and interprets the question via a request processing pipeline 108, and provides a response to the cognitive system user, e.g., cognitive system user 110, containing one or more answers to the question. In some embodiments, the cognitive system 100 provides a response to users in a ranked list of candidate answers while in other illustrative embodiments, the cognitive system 100 provides a single final answer or a combination of a final answer and ranked listing of other candidate answers.

The cognitive system 100 implements the request processing pipeline 108, which comprises a plurality of stages for processing an input question and the corpus of data 106. The request processing pipeline 108 generates answers for the input question based on the processing of the input question and the corpus of data 106. The request processing pipeline 108 will be described in greater detail hereafter with regard to FIG. 4.

In some illustrative embodiments, the cognitive system 100 may be the IBM Watson™ cognitive system available from International Business Machines Corporation of Armonk, N.Y., which is augmented with the mechanisms of the illustrative embodiments described hereafter. As outlined previously, a request processing pipeline of the IBM Watson™ cognitive system receives an input question which it then parses to extract the major features of the question, which in turn are then used to formulate queries that are applied to the corpus of data. Based on the application of the queries to the corpus of data, a set of hypotheses, or candidate answers to the input question, are generated by looking across the corpus of data for portions of the corpus of data that have some potential for containing a valuable response to the input question. The request processing pipeline of the IBM Watson™ cognitive system then performs deep analysis on the language of the input question and the language used in each of the portions of the corpus of data found during the application of the queries using a variety of reasoning algorithms.

The scores obtained from the various reasoning algorithms are then weighted against a statistical model that summarizes a level of confidence that the request processing pipeline of the IBM Watson™ cognitive system has regarding the evidence that the potential response, i.e. candidate answer, is inferred by the question. This process is be repeated for each of the candidate answers to generate ranked listing of candidate answers which may then be presented to the user that submitted the input question, or from which a final answer is selected and presented to the user. More information about the request processing pipeline of the IBM Watson™ cognitive system may be obtained, for example, from the IBM Corporation website, IBM Redbooks, and the like. For example, information about the request processing pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As noted above, while the input to the cognitive system 100 from a client device may be posed in the form of a natural language question, the illustrative embodiments are not limited to such. Rather, the input question may in fact be formatted or structured as any suitable type of request which may be parsed and analyzed using structured and/or unstructured input analysis, including but not limited to the natural language parsing and analysis mechanisms of a cognitive system such as the IBM Watson™ cognitive system, to determine the basis upon which to perform cognitive analysis and providing a result of the cognitive analysis. In the case of a healthcare based cognitive system, this analysis may involve processing patient medical records, medical guidance documentation from one or more corpora, and the like, to provide a healthcare oriented cognitive system result.

In the context of the present invention, cognitive system 100 may provide a cognitive functionality for assisting with healthcare based operations. For example, depending upon the particular implementation, the healthcare based operations may comprise patient diagnostics, medical treatment recommendation systems, medical practice management systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a medical treatment recommendation system that analyzes a patient's EMR in relation to medical guidelines and other medical documentation in a corpus of information to generate a recommendation as to how to treat a medical malady or medical condition of the patient. A patient's EMR may contain structured and unstructured information that comes from an Electronic Health Record (EHR) system, which may further be augmented with information from a clinician when using a clinical decision support system In particular, the cognitive system 100 implements an entity relation detection component 120 for enhancing a set of entity relationships by connecting multiple sentences and drawing a knowledge graph based on document structure. Entity relation detection component 120 draws a hierarchy of containers to identify entities that are related to each other. That is, entity relation detection component 120 draws a bigger picture for a patient case, rather than working on a sentence level. Entity relation detection component 120 takes a non-standard set of sentences that are in non-obvious form (e.g., lists, sub-sections, hierarchical structures) and dynamically represents the relationships across the sentences and across the lists. Entity relation detection component 120 generates a container representation of entity relationships and produces parseable grammatical sentences based on the knowledge graph representation. Thus, entity relation detection component 120 is capable of obtaining complete entities from non-standard text, such as clinical notes or medical report in an EMR.

In one embodiment, entity relation detection component 120 stores the generated grammatical sentences to the corpus, either as annotations to the EMR or as a separate document. Thus, entity relation detection component 120 creates a verbose EMR, which provides sentence-based insights that can be parsed by a decision support system. Entity relation detection component 120 may store the verbose EMR in corpus 106 or in a separate corpus specifically for insight analysis by an NLP processor and insight generator.

A verbose EMR is an electronic medical record with parseable sentences generated based on the hierarchical structure of an unstructured text portion of the EMR. The verbose EMR contains sentences that are parseable and more accurate than the original information. The sentences in the EMR communicate the contextual relationships between relationships based on the hierarchical structure of the text.

Figure 2:
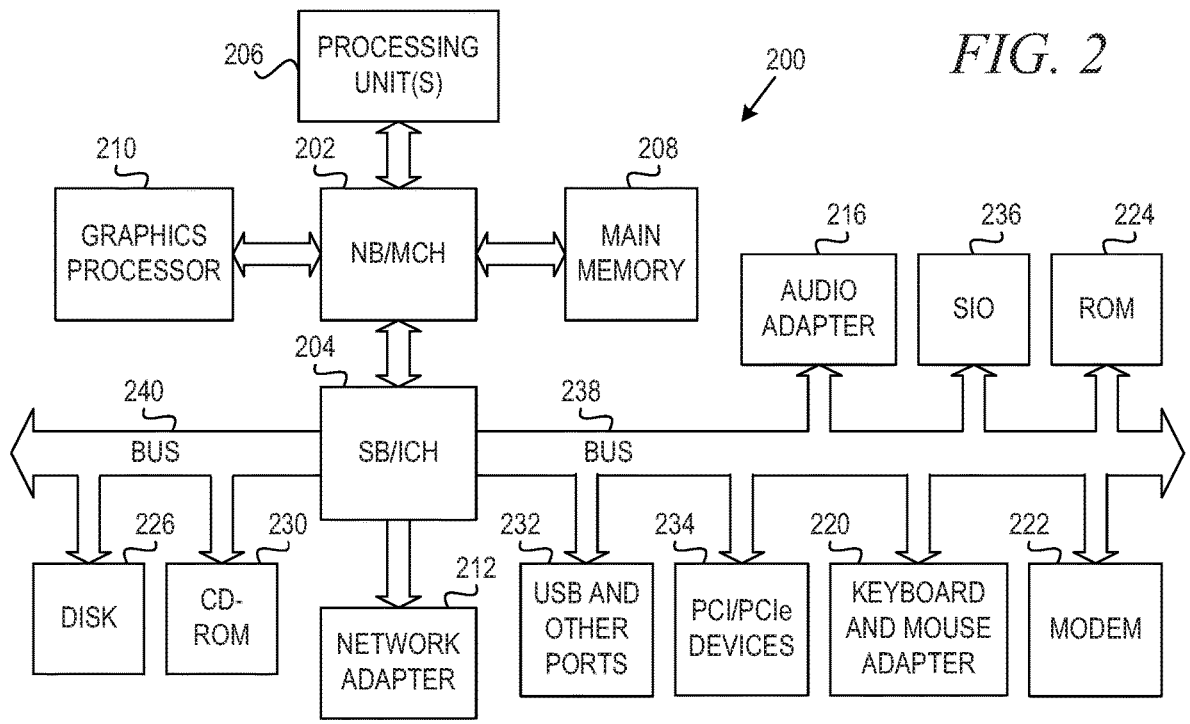
FIG. 2 is a block diagram of an example data processing system in which aspects of the illustrative embodiments are implemented.

FIG. 2 is a block diagram of an example data processing system in which aspects of the illustrative embodiments are implemented. Data processing system 200 is an example of a computer, such as server 104 or client 110 in FIG. 1, in which computer usable code or instructions implementing the processes for illustrative embodiments of the present invention are located. In one illustrative embodiment, FIG. 2 represents a server computing device, such as a server 104, which implements an NL processing system 100 and NL system pipeline 108 augmented to include the additional mechanisms of the illustrative embodiments described hereafter.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 8®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p® computer system, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
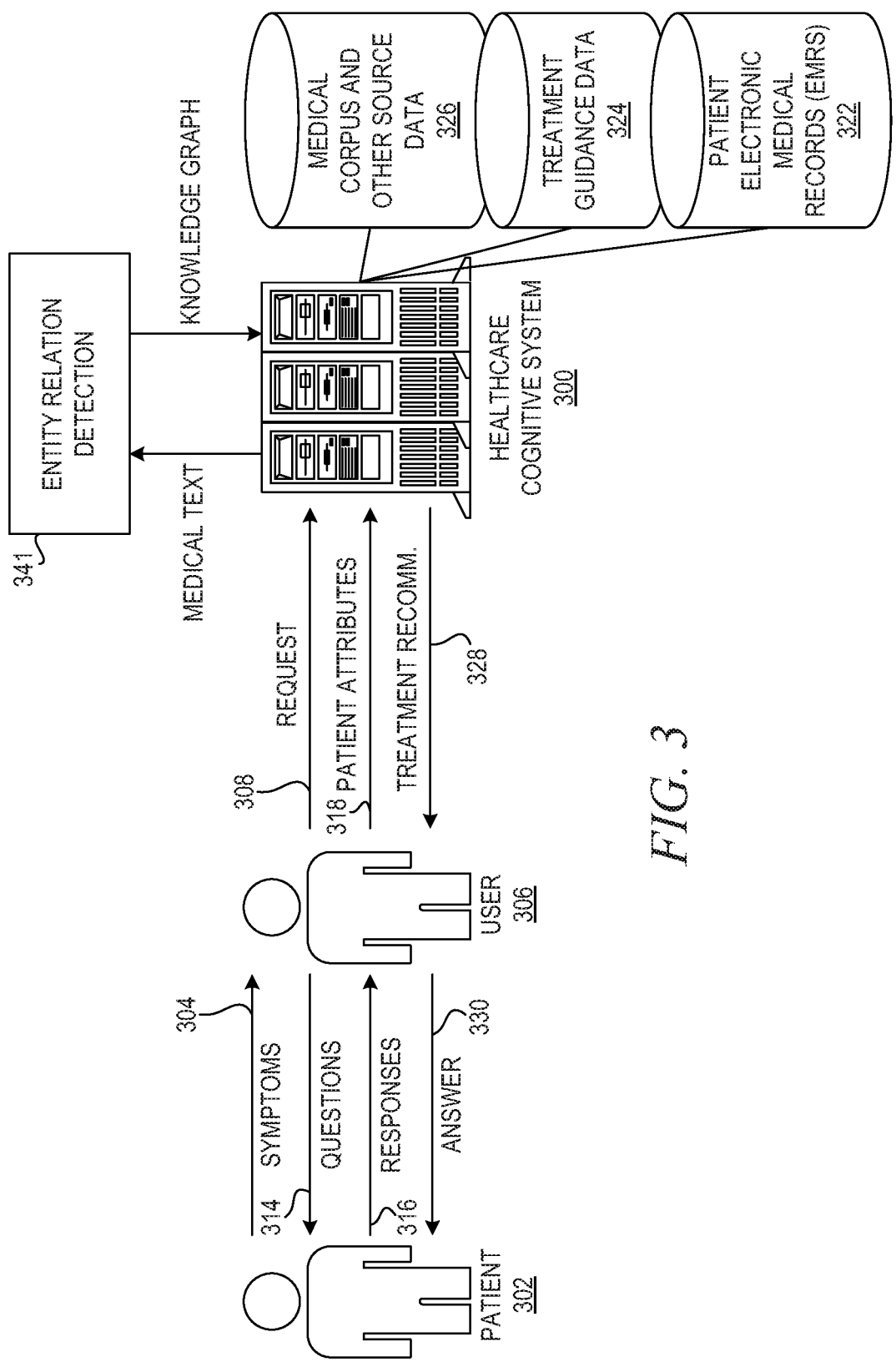
FIG. 3 is an example diagram illustrating an interaction of elements of a healthcare cognitive system in accordance with one illustrative embodiment.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide medical treatment recommendations for patients. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical malady or condition to a user 306, such as a healthcare practitioner, technician, or the like. The user 306 may interact with the patient 302 via a question 314 and response 316 exchange where the user gathers more information about the patient 302, the symptoms 304, and the medical malady or condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™ wearable device, a wearable heart monitor, or any other medical equipment that may monitor one or more medical characteristics of the patient 302. In some cases such medical equipment may be medical equipment typically used in hospitals or medical centers to monitor vital signs and medical conditions of patients that are present in hospital beds for observation or medical treatment.

In response, the user 302 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a treatment recommendation 328 to the user 306 to assist the user 306 in treating the patient 302 based on their reported symptoms 304 and other information gathered about the patient 302 via the question 314 and response 316 process and/or medical equipment monitoring/data gathering. The healthcare cognitive system 300 operates on the request 308 and patient attributes 318 utilizing information gathered from the medical corpus and other source data 326, treatment guidance data 324, and the patient EMRs 322 associated with the patient 302 to generate one or more treatment recommendation 328. The treatment recommendations 328 may be presented in a ranked ordering with associated supporting evidence, obtained from the patient attributes 318 and data sources 322-326, indicating the reasoning as to why the treatment recommendation 328 is being provided and why it is ranked in the manner that it is ranked.

For example, based on the request 308 and the patient attributes 318, the healthcare cognitive system 300 may operate on the request, such as by using a QA pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate treatment recommendations (or answers to the input question), and score these candidate treatment recommendations based on supporting evidence found in the data sources 322-326. In the depicted example, the patient EMRs 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise varied demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed to generate treatment recommendations 328.

The treatment guidance data 324 provides a knowledge base of medical knowledge that is used to identify potential treatments for a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

In some cases, such treatment guidance data 324 may be provided in the form of rules that indicate the criteria required to be present, and/or required not to be present, for the corresponding treatment to be applicable to a particular patient for treating a particular symptom or medical malady/condition. For example, the treatment guidance data 324 may comprise a treatment recommendation rule that indicates that for a treatment of Decitabine, strict criteria for the use of such a treatment is that the patient 302 is less than or equal to 60 years of age, has acute myeloid leukemia (AML), and no evidence of cardiac disease. Thus, for a patient 302 that is 59 years of age, has AML, and does not have any evidence in their patient attributes 318 or patient EMRs indicating evidence of cardiac disease, the following conditions of the treatment rule exist:

Age<=60 years=59 (MET);

Patient has AML=AML (MET); and

Cardiac Disease=false (MET)

Since all of the criteria of the treatment rule are met by the specific information about this patient 302, then the treatment of Decitabine is a candidate treatment for consideration for this patient 302. However, if the patient had been 69 years old, the first criterion would not have been met and the Decitabine treatment would not be a candidate treatment, for consideration for this patient 302. Various potential treatment recommendations may be evaluated by the healthcare cognitive system 300 based on ingested treatment guidance data 324 to identify subsets of candidate treatments for further consideration by the healthcare cognitive system 300 by scoring such candidate treatments based on evidential data obtained from the patient EMRs 322 and medical corpus and other source data 326.

For example, data mining processes may be employed to mine the data in sources 322 and 326 to identify evidential data supporting and/or refitting the applicability of the candidate treatments to the particular patient 302 as characterized by the patient's patient attributes 318 and EMRs 322. For example, for each of the criteria of the treatment rule, the results of the data mining provides a set of evidence that supports giving the treatment in the cases where the criterion is "MET" and in cases where the criterion is "NOT MET." The healthcare cognitive system 300 processes the evidence in accordance with various cognitive logic algorithms to generate a confidence score for each candidate treatment recommendation indicating a confidence that the corresponding candidate treatment recommendation is valid for the patient 302. The candidate treatment recommendations may then be ranked according to their confidence scores and presented to the user 306 as a ranked listing of treatment recommendations 328. In some cases, only a highest ranked, or final answer, is returned as the treatment recommendation 328. The treatment recommendation 328 may be presented to the user 306 in a manner that the underlying evidence evaluated by the healthcare cognitive system 300 may be accessible, such as via a drilldown interface, so that the user 306 may identify the reasons why the treatment recommendation 328 is being provided by the healthcare cognitive system 300.

In accordance with the illustrative embodiments herein, the healthcare cognitive system 300 is augmented to operate with, implement, or include entity relation detection component 341 for generating container-based knowledge graphs for determining entity relationships in medical text. While the above description describes a general healthcare cognitive system 300 that may operate on specifically configured treatment recommendation rules, the mechanisms of the illustrative embodiments modify such operations to utilize the entity relation detection component 341, which is medical malady independent or agnostic and operates in the manner previously described above with particular reference to FIGS. 5-14 below.

Thus, in response to the healthcare cognitive system 300 receiving the request 308 and patient attributes 318, the healthcare cognitive system 300 may retrieve the patient's EMR data from source(s) 322. This information is provided to entity relation detection component 341, which enhances entity relationships by connecting multiple sentences and drawing a knowledge graph based on document structure. Entity relation detection component 341 takes a non-standard set of sentences that are in non-obvious form (e.g., lists, sub-sections, hierarchical structures) and dynamically represents the relationships across the sentences and across the lists. Entity relation detection component 341 generates a container representation of entity relationships and produces parseable grammatical sentences based on the knowledge graph representation.

In one embodiment, entity relation detection component 341 stores the generated grammatical sentences to the corpus, either as annotations to the EMR or as a separate document. Thus, entity relation detection component 341 creates a verbose EMR, which provides sentence-based insights that can be parsed by a decision support system. Entity relation detection component 341 may store the verbose EMR in patient electronic medical records 322 or in medical corpus 326 for insight analysis by an NLP processor and insight generator.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 treatment recommendations 328 from the healthcare cognitive system 300 directly based on the symptoms 304 provided by the patient 302 to the healthcare cognitive system 300. Moreover, the healthcare cognitive system 300 may actually have logic for automatically posing questions 314 to the patient 302 and receiving responses 316 from the patient 302 to assist with data collection for generating treatment recommendations 328. In the latter case, the user 306 may operate based on only information previously gathered and present in the patient EMR 322 by sending a request 308 along with patient attributes 318 and obtaining treatment recommendations in response from the healthcare cognitive system 300. Thus, the depiction in FIG. 3 is only an example and should not be interpreted as requiring the particular interactions depicted when many modifications may be made without departing from the spirit and scope of the present invention.

As mentioned above, the healthcare cognitive system 300 may include a request processing pipeline, such as request processing pipeline 108 in FIG. 1, which may be implemented, in some illustrative embodiments, as a Question Answering (QA) pipeline. The QA pipeline may receive an input question, such as "what is the appropriate treatment for patient P?" or a request, such as "diagnose and provide a treatment recommendation for patient P."

Figure 4:
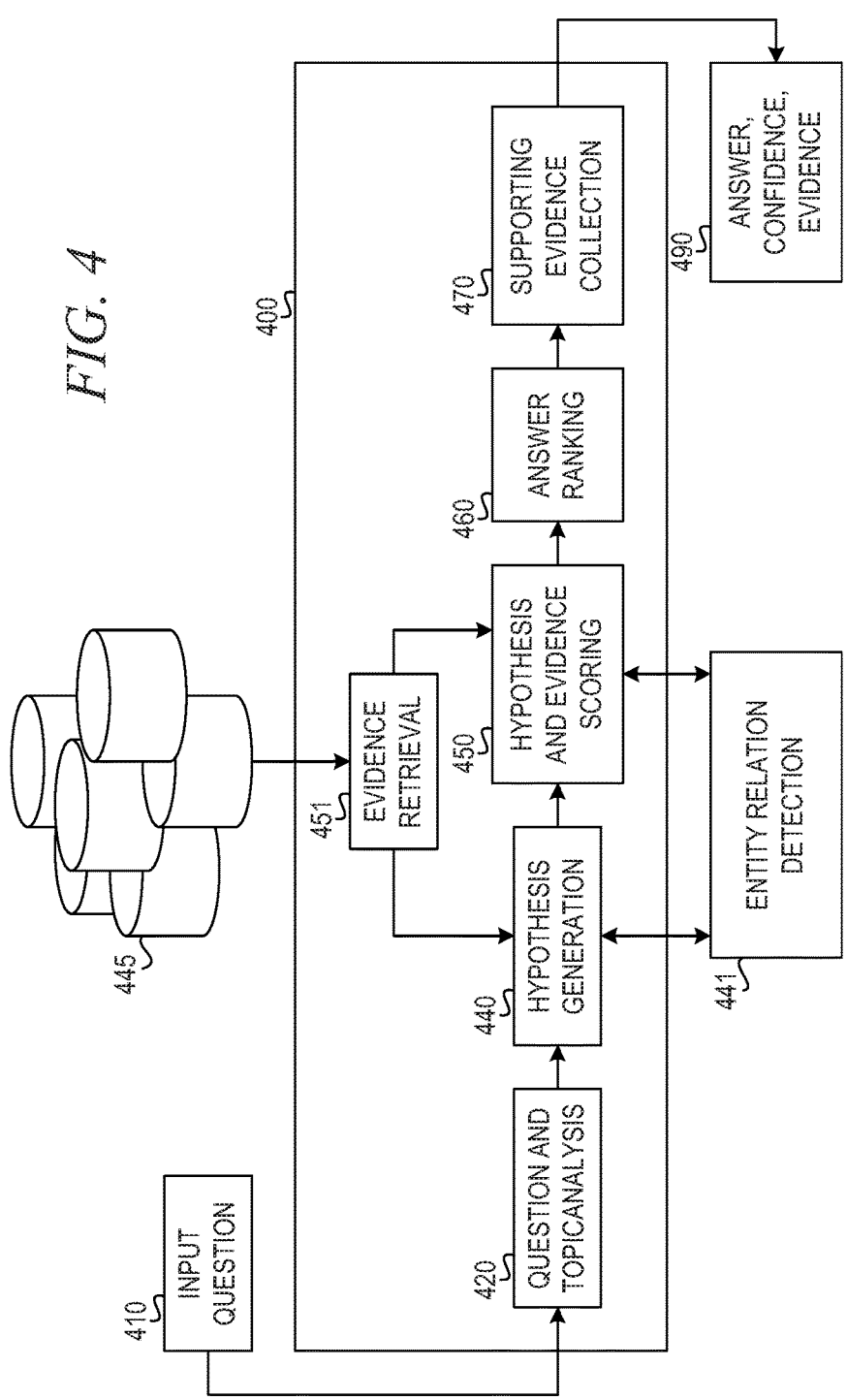
FIG. 4 illustrates a request processing pipeline for processing an input question in accordance with one illustrative embodiment.

FIG. 4 illustrates a request processing pipeline for processing an input question in accordance with one illustrative embodiment. The request processing pipeline of FIG. 4 may be implemented, for example, as request processing pipeline 108 of cognitive processing system 100 in FIG. 1. It should be appreciated that the stages of the request processing pipeline shown in FIG. 4 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems. The request processing pipeline of FIG. 4 is augmented, for example, in one or more of the stages to implement the improved mechanism of the illustrative embodiments described hereafter, additional stages may be provided to implement the improved mechanism, or separate logic from the pipeline 400 may be provided for interfacing with the pipeline 400 and implementing the improved functionality and operations of the illustrative embodiments.

In the depicted example, request processing pipeline 400 is implemented in a Question Answering (QA) system. The description that follows refers to the cognitive system pipeline or request processing pipeline as a QA system; however, aspects of the illustrative embodiments may be applied to other request processing systems, such as Web search engines that return semantic passages from a corpus of documents.

As shown in FIG. 4, the request processing pipeline 400 comprises a plurality of stages 410-490 through which the cognitive system operates to analyze an input question and generate a final response. In an initial question input stage, the QA system receives an input question 410 that is presented in a natural language format. That is, user inputs, via a user interface, an input question for which the user wishes to obtain an answer, e.g., "What medical treatments for diabetes are applicable to a 60 year old patient with cardiac disease?" In response to receiving the input question 410, the next stage of the QA system pipeline 400, i.e. the question and topic analysis stage 420, analyzes the input question using natural language processing (NLP) techniques to extract major elements from the input question, and classify the major elements according to types, e.g., names, dates, or any of a plethora of other defined element types. For example, in the example question above, the term "who" may be associated with a topic for "persons" indicating that the identity of a person is being sought, "Washington" may be identified as a proper name of a person with which the question is associated, "closest" may be identified as a word indicative of proximity or relationship, and "advisors" may be indicative of a noun or other language topic. Similarly, in the previous question "medical treatments" may be associated with pharmaceuticals, medical procedures, holistic treatments, or the like, "diabetes" identifies a particular medical condition, "60 years old" indicates an age of the patient, and "cardiac disease" indicates an existing medical condition of the patient.

In addition, the extracted major features include key words and phrases classified into question characteristics, such as the focus of the question, the lexical answer type (LAT) of the question, and the like. As referred to herein, a lexical answer type (LAT) is a word in, or a word inferred from, the input question that indicates the type of the answer, independent of assigning semantics to that word. For example, in the question "What maneuver was invented in the 1500 s to speed up the game and involves two pieces of the same color?," the LAT is the string "maneuver." The focus of a question is the part of the question that, if replaced by the answer, makes the question a standalone statement. For example, in the question "What drug has been shown to relieve the symptoms of attention deficit disorder with relatively few side effects?," the focus is "What drug" since if this phrase were replaced with the answer it would generate a true sentence, e.g., the answer "Adderall" can be used to replace the phrase "What drug" to generate the sentence "Adderall has been shown to relieve the symptoms of attention deficit disorder with relatively few side effects." The focus often, but not always, contains the LAT. On the other hand, in many cases it is not possible to infer a meaningful LAT from the focus.

Referring again to FIG. 4, the identified major elements of the question are then used during a hypothesis generation stage 440 to decompose the question into one or more search queries that are applied to the corpora of data/information 445 in order to generate one or more hypotheses. The queries are applied to one or more text indexes storing information about the electronic texts, documents, articles, websites, and the like, that make up the corpus of data/information, e.g., the corpus of data 106 in FIG. 1. The queries are applied to the corpus of data/information at the hypothesis generation stage 440 to generate results identifying potential hypotheses for answering the input question, which can then be evaluated. That is, the application of the queries results in the extraction of portions of the corpus of data/information matching the criteria of the particular query. These portions of the corpus are then analyzed and used in the hypothesis generation stage 440, to generate hypotheses for answering the input question 410. These hypotheses are also referred to herein as "candidate answers" for the input question. For any input question, at this stage 440, there may be hundreds of hypotheses or candidate answers generated that may need to be evaluated.

Entity relation detection component 441 analyzes statements in documents (e.g., EMRs) within corpora 445 and extracts normalized features for the purpose of treatment recommendations or clinical decision support. Entity relation detection component 441 utilizes container-based knowledge graphs to find entity relationships across sentences. Entity relation detection component 441 builds a model in the system as if the entities are connected in a physician's mind. The closer the knowledge graph is to the model that the physician has, the more accurate treatment recommendation can be made. The mechanism for generating container-based knowledge graphs and determining entity relations in medical text is described in further detail below with reference to FIGS. 5-14.

In one embodiment, entity relation detection component 441 stores the generated grammatical sentences to the corpus, either as annotations to the EMR or as a separate document. Thus, entity relation detection component 441 creates a verbose EMR, which provides sentence-based insights that can be parsed by a decision support system. Entity relation detection component 441 may store the verbose EMR in corpus 445 or in a separate corpus specifically for insight analysis by an NLP processor and insight generator.

The QA system pipeline 400, in stage 450, then performs a deep analysis and comparison of the language of the input question and the language of each hypothesis or "candidate answer," as well as performs evidence scoring to evaluate the likelihood that the particular hypothesis is a correct answer for the input question. This involves evidence retrieval 451, which retrieves passages from corpora 445. Hypothesis and evidence scoring phase 450 uses a plurality of scoring algorithms, each performing a separate type of analysis of the language of the input question and/or content of the corpus that provides evidence in support of, or not in support of, the hypothesis. Each scoring algorithm generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed. In general, however, these algorithms look for particular terms, phrases, or patterns of text that are indicative of terms, phrases, or patterns of interest and determine a degree of matching with higher degrees of matching being given relatively higher scores than lower degrees of matching.

It should be appreciated that this is just one simple example of how scoring can be performed. Many other algorithms of various complexities may be used to generate scores for candidate answers and evidence without departing from the spirit and scope of the present invention.

In answer ranking stage 460, the scores generated by the various scoring algorithms are synthesized into confidence scores or confidence measures for the various hypotheses. This process involves applying weights to the various scores, where the weights have been determined through training of the statistical model employed by the QA system and/or dynamically updated. For example, the weights for scores generated by algorithms that identify exactly matching terms and synonyms may be set relatively higher than other algorithms that evaluate publication dates for evidence passages.

The weighted scores are processed in accordance with a statistical model generated through training of the QA system that identifies a manner by which these scores may be combined to generate a confidence score or measure for the individual hypotheses or candidate answers. This confidence score or measure summarizes the level of confidence that the QA system has about the evidence that the candidate answer is inferred by the input question, i.e. that the candidate answer is the correct answer for the input question.

In accordance with the illustrative embodiments, the candidate answers may depend on an accurate determination of entity relations. For example, if the question asks for a healthcare recommendation, and the candidate answers are based on natural language clinical notes in electronic medical records (EMR), then some of the candidate answers may be based on relationships between entities in the clinical notes. As described above, entity relation detection component 441 analyzes statements in documents (e.g., EMRs) within corpora 445, generates container-based knowledge graphs, and determines entity relations based on the knowledge graphs. The resulting confidence scores of answers will take into account the results of entity relation detection component 441.

In one embodiment, entity relation detection component 441 stores the generated grammatical sentences to the corpus, either as annotations to the EMR or as a separate document. Thus, entity relation detection component 441 creates a verbose EMR, which provides sentence-based insights that can be parsed by a decision support system. In this embodiment, hypotheses generation stage 440 may apply queries to these verbose EMRs to generate candidate answers.

The resulting confidence scores or measures are processed by answer ranking stage 460, which compares the confidence scores and measures to each other, compares them against predetermined thresholds, or performs any other analysis on the confidence scores to determine which hypotheses/candidate answers are the most likely to be the correct answer to the input question. The hypotheses/candidate answers are ranked according to these comparisons to generate a ranked listing of hypotheses/candidate answers (hereafter simply referred to as "candidate answers").

Supporting evidence collection phase 470 collects evidence that supports the candidate answers from answer ranking phase 460. From the ranked listing of candidate answers in stage 460 and supporting evidence from supporting evidence collection stage 470, NL system pipeline 400 generates a final answer, confidence score, and evidence 480, or final set of candidate answers with confidence scores and supporting evidence, and outputs answer, confidence, and evidence 490 to the submitter of the original input question 410 via a graphical user interface or other mechanism for outputting information.

Figure 5:
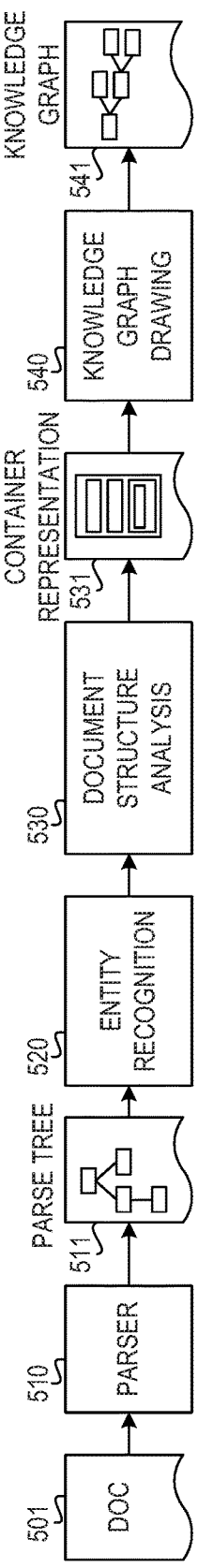
FIG. 5 depicts an example block diagram of a mechanism for determining entity relations in non-narrative text in accordance with an illustrative embodiment.

FIG. 5 depicts an example block diagram of a mechanism for determining entity relations in medical text in accordance with an illustrative embodiment. Electronic medical record (EMR) 501 for a given patient is provided to parser component 510, which obtains a parse tree 511 for every sentence of a patient note in EMR 501. Entity recognition component 520 recognizes entities in the document. In one embodiment, entity recognition component 520 compares words or terms in EMR 501 to Unified Medical Language System (UMLS) dictionary, for example. The UMLS is a compendium of many controlled vocabularies in the biomedical sciences. It provides a mapping structure among these vocabularies and, thus, allows one to translate among the various terminology systems; it may also be viewed as a comprehensive thesaurus and ontology of biomedical concepts. UMLS further provides facilities for natural language processing. It is intended to be used mainly by developers of systems in medical informatics.

Figure 6A:
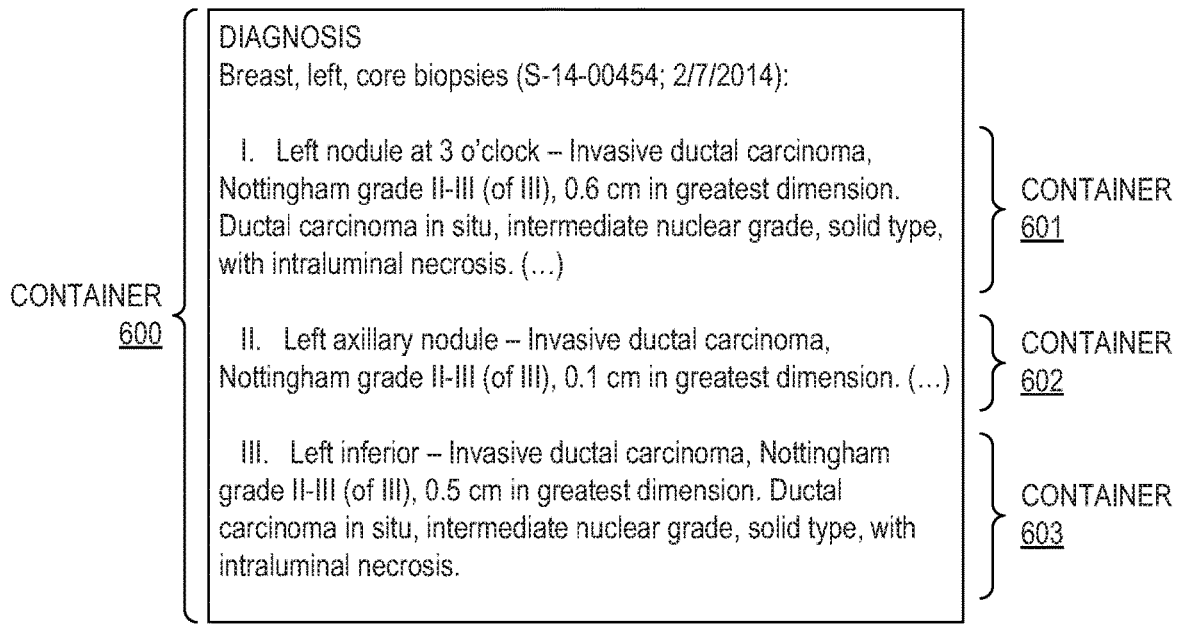
FIG. 6A is an example clinical note section of an electronic medical record in accordance with an illustrative embodiment.
Figure 6B:
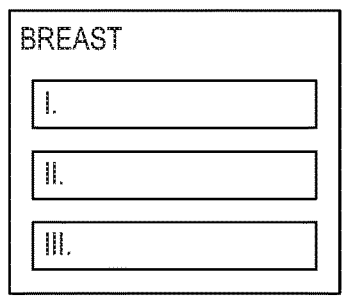
FIG. 6B depicts an example container representation of a clinical note in accordance with an illustrative embodiment.

Document structure analysis component 530 obtains a container representation of the document 531 (e.g., EMR 501 or a particular clinical note in EMR 501) based on the document structure. EMR 501 includes structured and unstructured content, including a plurality of clinical notes in natural language. FIG. 6A is an example clinical note section of an electronic medical record in accordance with an illustrative embodiment. As shown in FIG. 6A, the clinical note itself is a container 600, which contains the text of the clinical note. The clinical note of FIG. 6A also includes multiple sub-sections, which document structure analysis component 530 recognizes as a list numbered with roman numerals. Document structure analysis component 530 treats these sub-sections as containers 601, 602, 603. Document structure analysis component 530 also recognizes that container 600 contains containers 601, 602, 603, thus generating a hierarchical container representation of the document. In accordance with one illustrative embodiment, document structure analysis component 530 places each sentence in the container based on its relative position in a hierarchical list. FIG. 6B depicts an example container representation of a clinical note in accordance with an illustrative embodiment.

Figure 7B:
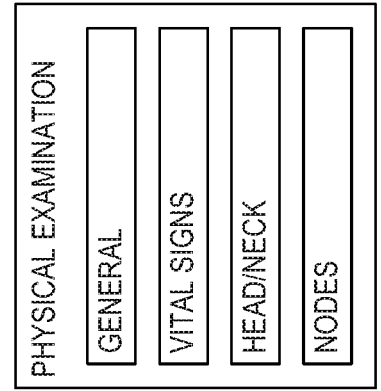
FIGS. 7A and 7B illustrate examples of clinical note section of an electronic medical record and a corresponding container representation of the clinical note in accordance with an illustrative embodiment.
Figure 7A:
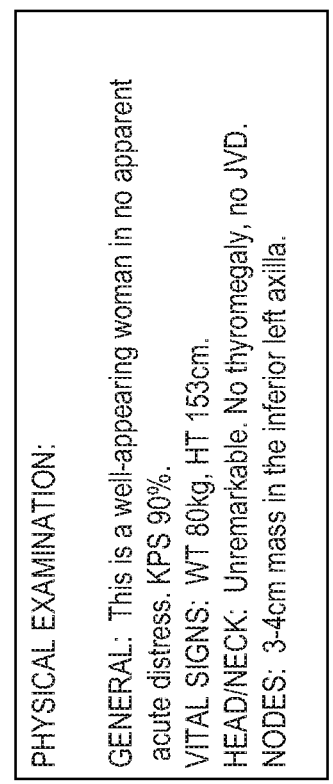

FIGS. 7A and 7B illustrate examples of clinical note section of an electronic medical record and a corresponding container representation of the clinical note in accordance with an illustrative embodiment. In the depicted examples, the clinical note section itself is a container, labeled "PHYSICAL EXAMINATION." This container also contains sub-sections, "GENERAL," "VITAL SIGNS," "HEAD/NECK," and "NODES," as indicated by the structure of the document. In one example embodiment, document structure analysis component 530 recognizes headings, lists, and the like. In this example, each section begins with a capitalized heading followed by a colon. Other common structures may be recognized by document structure analysis component 530. In the depicted example, document structure analysis component 530 creates a container for each sub-section within the clinical note container, thus creating a hierarchical container representation, as shown in FIG. 7B.

Knowledge graph drawing component 540 draws knowledge graph 541 utilizing detected entities and container information finding entity relations across sentences. Knowledge graph drawing component 540 denotes the parent in the hierarchical list and finds the main subject or concept type. Knowledge graph drawing component 540 parses a sentence to find subject and nouns and performs a lexical entity detection for major concept types for the domain. Knowledge graph drawing component 540 correlates the key concept found based on the set of entities detected in the child sentences and determines a relevance score based on similarity concept matching using UMLS. For sections knowledge graph drawing component 540 can predefine the type of concepts that are key based on the section type or sections. Knowledge graph drawing component 540 sets the parent concept and its parts of speech as the main root element (container level).

Based on parts of speech (qualifier, noun, pronoun, subject, etc.) of all child entities and that sentence relationship, knowledge graph drawing component 540 deduces a potential relationship to the container level concept. For each entity in the child sentence, knowledge graph drawing component 540 finds relevance to the subject by concept type and co-occurrence (similarity matching or concept matching). Knowledge graph drawing component 540 generates a relevance score for the relationship and relationship type (e.g., UMLS concept matcher).

Figure 8:
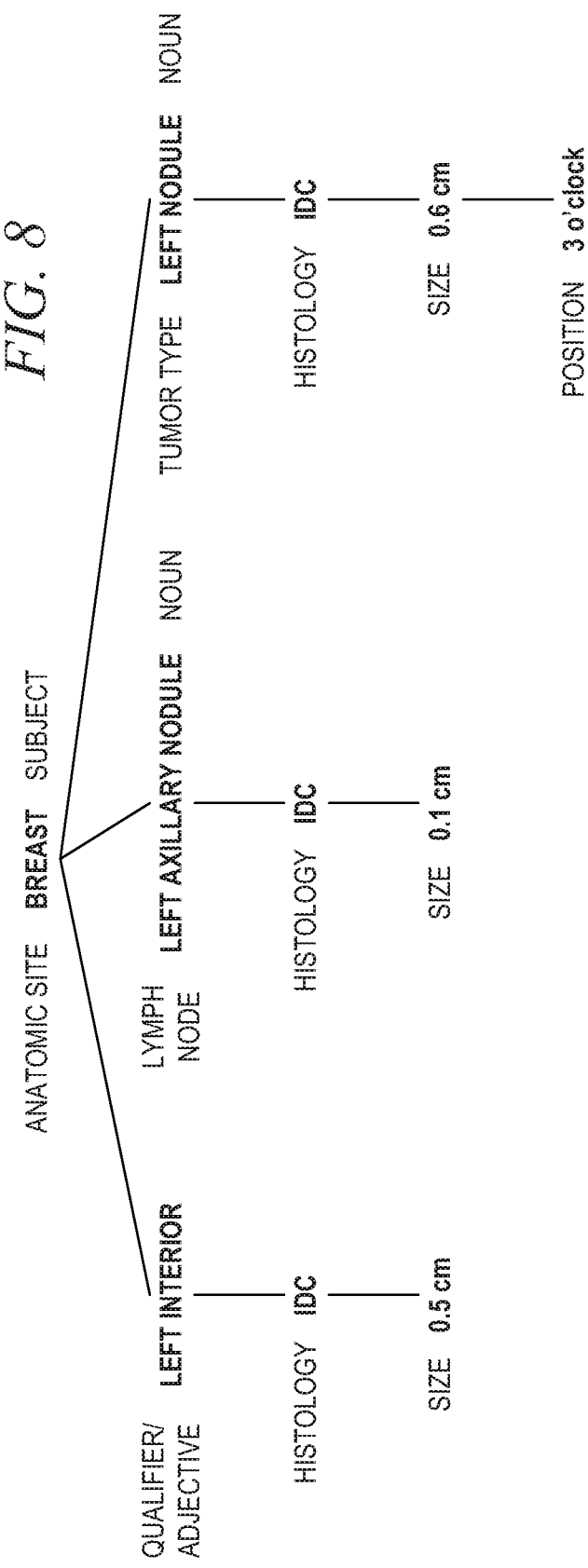
FIG. 8 depicts an example knowledge graph generated form a container representation in accordance with an illustrative embodiment.

Knowledge graph drawing component 540 connects the parent node to the child node with parts of speech and concept type metadata. Knowledge graph drawing component 540 then repeats the above process at each level in the container hierarchical representation. FIG. 8 depicts an example knowledge graph generated form a container representation in accordance with an illustrative embodiment.

Sentence generation component 550 creates a grammatical representation of discovered entity relationships across sentences using templates. Sentence generation component 550 iterates over the nodes in the knowledge graph for each path in the graph. From root to leaf, sentence generation component 550 utilizes a grammatical template to generate a sentence. Note that there may be multiple sentences from the root until a leaf node is reached. Sentence generation is based on sentence similarity with other text with the same entities and part-of-speech type placement in the sentence.

Figure 9:
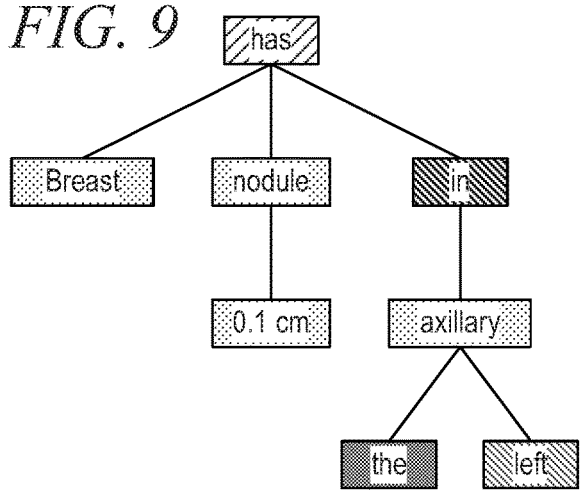
FIG. 9 depicts an example parse tree generated from a knowledge graph in accordance with an illustrative embodiment.

Sentence generation component 550 gets parse trees of larger sentences created in the previous step. Sentence generation component 550 ranks the sentences based on English Slot Grammar (ESG) parse score. FIG. 9 depicts an example parse tree generated from a knowledge graph in accordance with an illustrative embodiment. In the depicted example, the template used for sentence generation is as follows: SUBJ has SIZE in LOC. A grammatical representation of the discovered entity relations in the example is as follows: Breast has 0.1 cm nodule in the left axillary.

The generated sentences may be more accurate than the original information in the EMR 501. Actually, the original information may not be parseable or may not make sense to a machine, thus the need for this representation of parseable medical sentences. In most situations, the hierarchical representation is vague and not specific, even if it is unstructured text, because there are not enough relations for a machine to understand compared to the context that a human may use. Using the formatting, the hierarchy and the relational context between the top entry and potential relationships, sentence generation component 550 can generate a more accurate sentence, which leads to more accurate insights that help a machine to understand the EMR better.

Subject matter expert (SME) feedback component 560 presents the grammatical representation of the discovered entity relations to a subject matter expert (SME). Based on feedback from the SME, SME feedback component 560 stores the grammatical representation, such as a natural language sentence or parse tree, within verbose EMR 561. In one embodiment, the SME feedback may comprise approval or rejection of a sentence. In another embodiment, the SME may modify the sentence to more accurately reflect the information and context in the EMR 501.

The present invention may be a system, a method, and/or a computer program product. The computer program product may include a computer readable storage medium (or media) having computer readable program instructions thereon for causing a processor to early out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 10:
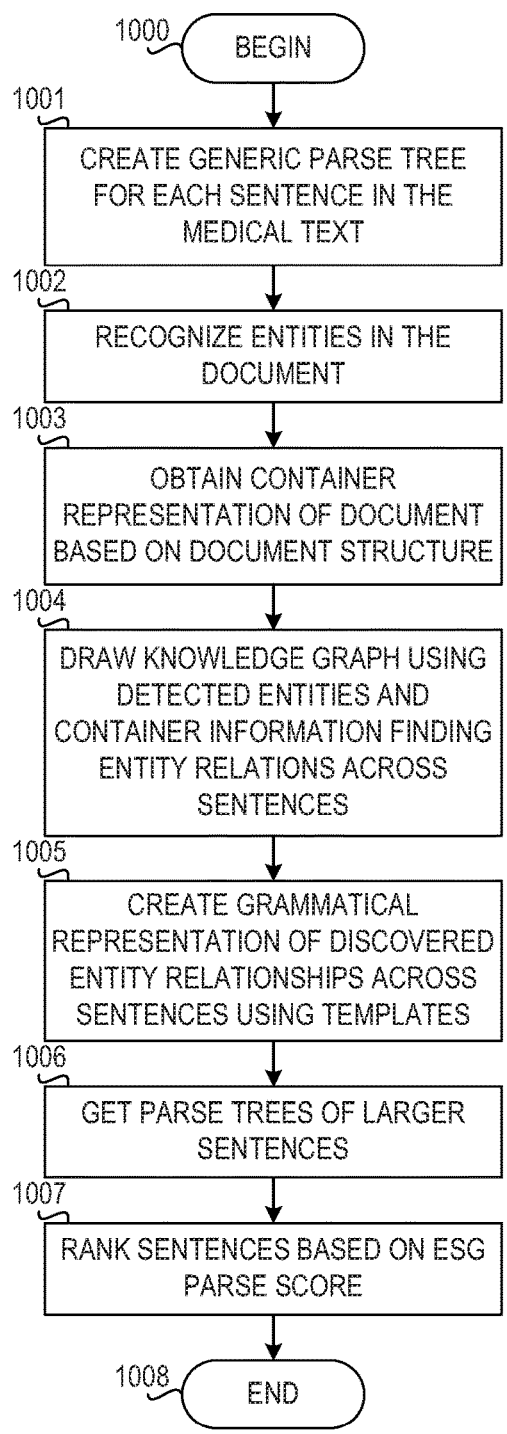
FIG. 10 is a flowchart illustrating operation of a mechanism for generating container-based knowledge graphs for determining entity relations in non-narrative text in accordance with an illustrative embodiment.

FIG. 10 is a flowchart illustrating operation of a mechanism for generating container-based knowledge graphs for determining entity relations in medical text in accordance with an illustrative embodiment. Operation begins for a given document of medical text, such as a clinical note in an electronic medical record (block 1000), and the mechanism creates a generic parse tree for each sentence in the medical text (block 1001). The mechanism recognizes entities in the document (block 1002). The mechanism then obtains a container representation of the document based on the document structure (block 1003). The mechanism obtains the container representation by creating containers based on a hierarchical list of the sections of the document and placing each sentence in a container based on its relative position in the hierarchical list.

The mechanism draws a knowledge graph utilizing detected entities and container information finding entity relations across sentences (block 1004). Operation of knowledge graph drawing is described in further detail below with reference to FIGS. 11-13.

The mechanism then creates a grammatical representation of the discovered entity relationships across sentences using templates (block 1005). The mechanism creates the grammatical representation by iterating over the nodes in the knowledge graph for each path in the graph. From root to leaf node, the mechanism utilizes a grammatical template to generate a sentence. There may be multiple sentences from the root to a leaf node. Sentence generation is based on sentence similarity to other text with the same entities and part-of-speech type placement in the sentence.

Next, the mechanism gets parse trees of the larger sentences created in block 1005 (block 1006). The mechanism ranks the sentences based on ESG parse score (block 1007). Thereafter, operation ends (block 1008).

Figure 11:
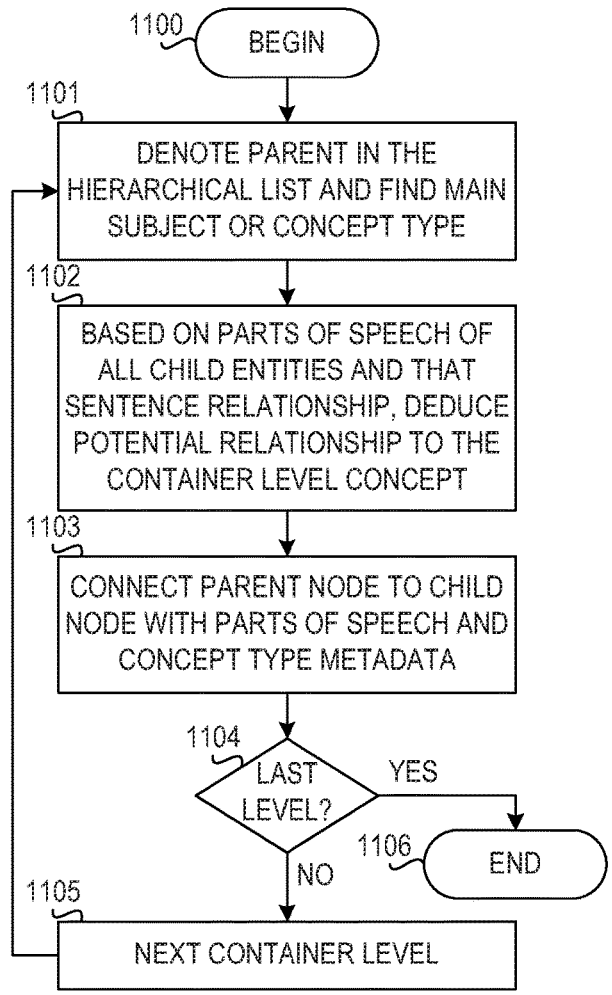
FIG. 11 is a flowchart illustrating operation of a mechanism for knowledge graph drawing in accordance with an illustrative embodiment.

FIG. 11 is a flowchart illustrating operation of a mechanism for knowledge graph drawing in accordance with an illustrative embodiment. Operation begins (block 1100), and the mechanism denotes the parent in the hierarchical list and finds the main subject or concept type (block 1101). Operation of a mechanism for denoting the parent is described in further detail below with reference to FIG. 12.

Based on parts of speech of all child entities and that sentence relationship, the mechanism deduces a potential relationship to the container level concept (block 1102). Operation of a mechanism for deducing a potential relationship is described with further detail below with reference to FIG. 13.

The mechanism then connects the parent node to the child node with parts of speech and concept type metadata (block 1103). The mechanism determines whether the container level is the last level in the container representation (block 1104). If the container level is not the last level, then the mechanism considers the next container level (block 1105), and operation returns to block 1101 to denote the parent in the next container level. If the container level is the last container level in the container representation in block 1104, then operation ends (block 1106).

FIG. 12 is a flowchart illustrating operation of a mechanism for denoting the parent in the hierarchical list and finding the main subject or concept type in accordance with an illustrative embodiment. Operation begins (block 1200), and the mechanism parses the sentence to find subjects and nouns and performs lexical entity detection for major concept types for the domain (block 1201). The mechanism correlates the key concept found based on the set of entities detected in the child sentences (block 1202). The mechanism also defines a relevance score based on similarity concept matching (block 1203). For sections the mechanism can predefine the type of concepts that are key based on the section type or sections. Next, the mechanism sets the parent concept and its parts of speech as the main root element for the container level (block 1204). Thereafter, operation ends (block 1205).

FIG. 13 is a flowchart illustrating operation of a mechanism for deducing potential relationships to a container level concept in accordance with an illustrative embodiment. Operation begins (block 1300), and for each entity in the child sentence, the mechanism finds a relevance to subject by concept type and co-occurrence (block 1301). Then, the mechanism generates a relevance score for the relationship and relationship type (block 1302). Thereafter, operation ends (block 1303).

FIG. 14 is a flowchart illustrating operation of a mechanism for generating a verbose electronic medical record in accordance with an illustrative embodiment. Operation begins (block 1400), and the mechanism presents a sentence generated from a container representation of an electronic medical record (EMR), as in block 1005 of FIG. 10, to a subject matter expert (SME) (block 1401). The mechanism may present the sentence as a natural language sentence or as a parse tree.

The mechanism determines whether the SME approves the sentence (block 1402). If the SME does not approve the sentence, then the mechanism receives feedback from the SME to modify or replace the sentence (block 1403). Thereafter, or if the SME approves the sentence in block 1402, the mechanism determines whether the sentence is the last sentence (block 1404). If the sentence is not the last sentence, then operation returns to block 1401 to present the next sentence to the SME. If the sentence is the last sentence from the EMR in block 1404, then the mechanism stores the sentences in the corpus as a verbose EMR (block 1405). A verbose EMR is an electronic medical record with parseable sentences generated based on the hierarchical structure of an unstructured text portion of the EMR. The verbose EMR contains sentences that are parseable and more accurate than the original information. The sentences in the EMR communicate the contextual relationships between relationships based on the hierarchical structure of the text. Thereafter, operation ends (block 1406).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Thus, the illustrative embodiments provide a mechanism that enhances the set of entity relationships by connecting multiple sentences and drawing a knowledge graph based on document structure. The mechanisms of the illustrative embodiments draw a hierarchy of containers to be able to identify entities that are related to each other and draw a higher level picture for the patient case rather than working on a sentence level. This produces a set of knowledge representations that are usually not provided in such a manner in texts and allows for reasoning and conjectures in decision making. The mechanisms of the illustrative embodiments obtain complete entities from non-standard forms of texts, which is very useful in medical texts and short-hand reports. Disease treatment systems can have better accuracy and utilize reports and forms to provide decision support (oncology, diabetes, lung, advisors).

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a clinical decision support system, the method comprising:

receiving, by the clinical decision support system, a plurality of patient electronic medical records (EMRs) for a patient from a plurality of different sources;

for a portion of a patient EMR of the plurality of patient EMRs, detecting, by an entity recognition component within the clinical decision support system, entities related across one or more sentences of the portion of the patient EMR and analyzing a document structure of the portion of the patient EMR to identify a hierarchical structure of the portion of the patient EMR;

generating, by a document structure analysis component executing within the clinical decision support system, a hierarchical container representation of the portion of the patient EMR based on the hierarchical structure, wherein the hierarchical container representation of the portion of the patient EMR contains a container for a sub-section of the portion of the patient EMR within the hierarchical container representation;

placing, by the document structure analysis component, each of the one or more sentences into the hierarchical container representation based on relative position within the hierarchical structure;

generating, by a knowledge graph drawing component executing within the clinical decision support system, a knowledge graph using the detected entities and the hierarchical container representation, wherein generating the knowledge graph comprises for a level of the hierarchical structure:

denoting a parent entity in the level and finding a main concept type of the parent entity;

based on a part of speech of a child entity and a sentence relationship, identifying a potential relationship between the child entity and the main concept type of the patent entity; and connecting the parent entity to the child entity with part-of-speech and concept type metadata to represent the relationship between the parent entity and the child entity in the knowledge graph, and generating, by the clinical decision support system, a treatment recommendation for the patient based on the knowledge graph, wherein generating the treatment recommendation comprises extracting, by the clinical decision support system, normalized features from the portion of the patient EMR based on the knowledge graph; generating, by the clinical decision support system, the treatment recommendation based on the extracted normalized features; and outputting, the clinical decision support system, the treatment recommendation for use in treating the patient.

2. The method of claim 1, wherein denoting the parent entity in the level and finding the main concept type of the parent entity comprise:

parsing a sentence in the level to find subjects and nouns;
performing lexical entity detection for major concept types for a domain of the patient EMR;
correlating a key concept found based on a set of entities detected in child sentences;
determining a relevance score based on similarity concept matching; and
setting the parent concept and its parts of speech as the main root element for the level.

3. The method of claim 1, wherein identifying the potential relationship to the main concept type comprises:

for each entity in a child sentence, determining relevance to a subject of the child sentence by concept type and co-occurrence; and
generating a relevance score for the potential relationship and a relationship type.

4. The method of claim 1, wherein the portion of the patent EMR is a clinical note or a medical report in the patient EMR.

5. A computer program product comprising a computer readable storage medium having a computer readable program stored therein, wherein the computer readable program comprises instructions, which when executed on a processor of a computing device causes the computing device to implement a clinical decision support system, wherein the computer readable program causes the computing device to:

receive, by the clinical decision support system, a plurality of patient electronic medical records (EMRs) for a patient from a plurality of different sources;

for a portion of a patient EMR of the plurality of patient EMRs, detect, by an entity recognition component within the clinical decision support system, entities related across one or more sentences of the portion of the patient EMR and analyze a document structure of the portion of the patient EMR to identify a hierarchical structure of the portion of the patient EMR;

generate, by a document structure analysis component executing within the clinical decision support system, a hierarchical container representation of the portion of the patient EMR based on the hierarchical structure, wherein the hierarchical container representation of the portion of the patient EMR contains a container for a sub-section of the portion of the patient EMR within the hierarchical container representation;

place, by the document structure analysis component, each of the one or more sentences into the hierarchical container representation based on relative position within the hierarchical structure;

generate, by a knowledge graph drawing component executing within the clinical decision support system, a knowledge graph using the detected entities and the hierarchical container representation, wherein generating the knowledge graph comprises for a level of the hierarchical structure:

denoting a parent entity in the level and finding a main concept type of the parent entity;

based on a part of speech of a child entity and a sentence relationship, identifying a potential relationship between the child entity and the main concept type of the patent entity; and connecting the parent entity to the child entity with part-of-speech and concept type metadata to represent the relationship between the parent entity and the child entity in the knowledge graph; and generate, by the clinical decision support system, a treatment recommendation for the patient based on the knowledge graph, wherein generating the treatment recommendation comprises extracting by the clinical decision support system, normalized features from the portion of the patient EMR based on the knowledge graph; generating, by the clinical decision support system, the treatment recommendation based on the extracted normalized features; and outputting, by the clinical decision support system, the treatment recommendation for use in treating the patient.

6. The computer program product of claim 5, wherein denoting the parent entity in the level and finding the main concept type of the parent entity comprise:

parsing a sentence in the level to find subjects and nouns;
performing lexical entity detection for major concept types for a domain of the patient EMR;
correlating a key concept found based on a set of entities detected in child sentences;
determining a relevance score based on similarity concept matching; and
setting the parent concept and its parts of speech as the main root element for the level.

7. The computer program product of claim 5, wherein identifying the potential relationship to the main concept type comprises:

for each entity in a child sentence, determining relevance to a subject of the child sentence by concept type and co-occurrence; and
generating a relevance score for the potential relationship and a relationship type.

8. The computer program product of claim 5, wherein the portion of the patent EMR is a clinical note or medical report in the patient EMR.

9. A computing device comprising:
a processor; and
a memory coupled to the processor, wherein the memory comprises instructions, which when executed on a processor of a computing device causes the computing device to implement a clinical decision support system, wherein the instructions cause the processor to:
receive, by the clinical decision support system, a plurality of patient electronic medical records (EMRs) for a patient from a plurality of different sources;
for a portion of a patient EMR of the plurality of patient EMRs, detect, by an entity recognition component within the clinical decision support system, entities related across one or more sentences of the portion of the patient EMR and analyze a document structure of the portion of the patient EMR to identify a hierarchical structure of the portion of the patient EMR;
generate, by a document structure analysis component executing within the clinical decision support system, a hierarchical container representation of the portion of the patient EMR based on the hierarchical structure, wherein the hierarchical container representation of the portion of the patient EMR contains a container for a sub-section of the portion of the patient EMR within the hierarchical container representation;
place, by the document structure analysis component, each of the one or more sentences into the hierarchical container representation based on relative position within the hierarchical structure;
generate, by a knowledge graph drawing component executing within the clinical decision support system, a knowledge graph using the detected entities and the hierarchical container representation, wherein generating the knowledge graph comprises for a level of the hierarchical structure:
denoting a parent entity in the level and finding a main concept type of the parent entity;
based on a part of speech of a child entity and a sentence relationship, identifying a potential relationship between the child entity and the main concept type of the patent entity; and
connecting the parent entity to the child entity with part-of-speech and concept type metadata to represent the relationship between the parent entity and the child entity in the knowledge graph; and
generate, by the clinical decision support system, a treatment recommendation for the patient based on the knowledge graph, wherein generating the treatment recommendation comprises extracting, by the clinical decision support system, normalized features from the portion of the patient EMR based on the knowledge graph; generating, by the clinical decision support system, the treatment recommendation based on the extracted normalized features; and outputting, by the clinical decision support system, the treatment recommendation for use in treating the patient.

10. The computing device of claim 9, wherein denoting the parent entity in the level and finding the main concept type of the parent entity comprise:

parsing a sentence in the level to find subjects and nouns;
performing lexical entity detection for major concept types for a domain of the patient EMR;
correlating a key concept found based on a set of entities detected in child sentences;
determining a relevance score based on similarity concept matching; and
setting the parent concept and its parts of speech as the main root element for the level.

11. The computing device of claim 9, wherein identifying the potential relationship to the main concept type comprises:
for each entity in a child sentence, determining relevance to a subject of the child sentence by concept type and co-occurrence; and
generating a relevance score for the potential relationship and a relationship type.

12. The computing device of claim 6, wherein the portion of the patent EMR is a clinical note or medical report in the patient EMR.

13. The method of claim 1, further comprising:
generating, by a sentence generation component executing within the clinical decision support system, a set of grammatical representations of one or more relationships identified within the container representation based on the container-based knowledge graph and using a set of predetermined grammatical templates, wherein the set of grammatical representations comprise natural language sentences; and
generating, by the clinical decision support system, a verbose EMR comprising the grammatical representations of the one or more relationships.

14. The method of claim 13, wherein generating the verbose EMR comprises:
presenting the set of grammatical representations of the one or more relationships to a subject matter expert; and
responsive to the subject matter expert approving a grammatical representation within the set of grammatical representations, storing the grammatical representation in association with the patient EMR to form the verbose EMR.

15. The method of claim 13, wherein generating the verbose EMR further comprises:
receiving feedback from the subject matter expert modifying a grammatical representation within the set of grammatical representations, the feedback forming a modified grammatical representation; and
storing the modified grammatical representation in association with the patient EMR to form the verbose EMR.

16. The computer program product of claim 5, wherein the computer readable program further causes the computing device to:
generate, by a sentence generation component executing within the clinical decision support system, a set of grammatical representations of one or more relationships identified within the container representation based on the container-based knowledge graph and using a set of predetermined grammatical templates, Wherein the set of grammatical representations comprise natural language sentences; and
generate, by the clinical decision support system, a verbose EMR comprising the grammatical representations of the one or more relationships.

17. The computer program product of claim 16, wherein generating the verbose EMR comprises:

presenting the set of grammatical representations of the one or more relationships to a subject matter expert; and responsive to the subject matter expert approving a grammatical representation within the set of grammatical representations, storing the grammatical representation in association with the patient EMR to form the verbose EMR.

18. The computer program product of claim 17, wherein generating the verbose EMR further comprises:

receiving feedback from the subject matter expert modifying a grammatical representation within the set of grammatical representations, the feedback forming a modified grammatical representation; and storing the modified grammatical representation in association with the patient EMR to form the verbose EMR.

19. The computing device of claim 9, wherein the instructions further cause the processor to:

generate, by a sentence generation component executing within the clinical decision support system, a set of grammatical representations of one or more relationships identified within the container representation based on the container-based knowledge graph and using a set of predetermined grammatical templates, wherein the set of grammatical representations comprise natural language sentences; and generate, by the clinical decision support system, a verbose EMR comprising the grammatical representations of the one or more relationships.

20. The computing device of claim 19, wherein generating the verbose EMR comprises:

presenting the set of grammatical representations of the one or more relationships to a subject matter expert;

responsive to the subject matter expert approving a grammatical representation within the set of grammatical representations, storing the grammatical representation in association with the patient EMR to form the verbose EMR;

receiving feedback from the subject matter expert modifying a grammatical representation within the set of grammatical representations, the feedback forming a modified grammatical representation; and storing the modified grammatical representation in association with the patient EMR to form the verbose EMR.

* * * * *